US012485296B2

(12) United States Patent
Landes et al.

(10) Patent No.: US 12,485,296 B2
(45) Date of Patent: Dec. 2, 2025

(54) METHODS FOR TREATING PATIENTS WITH PARALYTIC COLON SYNDROME

(71) Applicants: Mark David Landes, Burlington, IA (US); Ana Sarcia, Florianopolis (BR)

(72) Inventors: Mark David Landes, Burlington, IA (US); Ana Sarcia, Florianopolis (BR)

( * ) Notice: Subject to any disclaimer, the term of this patent is extended or adjusted under 35 U.S.C. 154(b) by 0 days.

(21) Appl. No.: 18/656,766

(22) Filed: May 7, 2024

(65) Prior Publication Data

US 2025/0345634 A1 Nov. 13, 2025

(51) Int. Cl.
*A61N 7/00* (2006.01)

(52) U.S. Cl.
CPC .................................... *A61N 7/00* (2013.01)

(58) Field of Classification Search
CPC ........................................................ A61N 7/00
See application file for complete search history.

(56) References Cited

U.S. PATENT DOCUMENTS

2011/0127732 A1* 6/2011 Mann ...................... B62B 5/026 280/5.2
2013/0041299 A1* 2/2013 Lacy ...................... A61H 21/00 601/46
2021/0402827 A1* 12/2021 Jacoby .................. B60C 11/005

* cited by examiner

*Primary Examiner* — Rochelle D Turchen
(74) *Attorney, Agent, or Firm* — Dunlap Bennett & Ludwig, PLLC

(57) ABSTRACT

Methods of treating patients with paralytic colon syndrome, wherein the method embodies devices that vibrate while supporting the patient. The method includes vibrating the patient in a supported position so as to urge an oscillating vertical displacement of approximately three to ten millimeters, wherein the vertical displacement is in a direction normal to a supporting surface of the supported position, and wherein the oscillation is at a frequency of at least five hertz and for a duration of at least ten minutes.

7 Claims, 4 Drawing Sheets

METHODS FOR TREATING PATIENTS WITH PARALYTIC COLON SYNDROME

BACKGROUND OF THE INVENTION

The present invention relates to treatments for patients with paralytic colon syndrome and, more particularly, to methods of treating patients with paralytic colon syndrome, wherein the method embodies devices that vibrate while supporting the patient.

Paralysis of bowel is a condition in which intestinal peristalsis slows down or completely stops. Paralyzed bowel is a serious condition and prompts immediate treatment to reduce the risk of complications. Paralytic bowel syndrome is often caused by bowel surgery. If electrolyte nutrition does not work, the solution is another bowel surgery. This often requires resecting intestines because feces have blocked the intestines.

Current medical treatments for paralytic colon syndrome include one of or a combination of the following: no food by mouth, whereby nutrition is provided intravenously, and medications are given to the patient so that the intestinal motility is resumed; and/or aggressive surgery to remove blockage whereas section of intestine is removed.

The nutritional electrolyte solution is at best a wait-and-see option; when it doesn't work, surgical intervention is required. The problem with bowel surgery is that it can cause paralytic bowel syndrome, and so the aggressive solution many times necessitates and leads to more complications and another bowel surgery.

As can be seen, there is a need for methods of treating patients with paralytic colon syndrome, wherein the method embodies devices that vibrate while supporting the patient.

SUMMARY OF THE INVENTION

The present invention offers a direct mechanical solution to the problem. The mechanical vibration generated by the present invention stimulates the intestine by shaking the whole body, where results can be seen in a few hours instead of many days.

The method embodied in the present invention provides mechanical stimulation for initiating peristaltic bowel movement. The mechanical vibration stimulates the intestine by shaking the whole body.

The stimulation treatment of the intestine to start the peristaltic movement can be accomplished by way of a device that accommodates the patient in a seated position, such as but not limited to a wheelchair, that provides vibration while the patient is using it. Other embodiments of the present invention embody a vibrating lounge chair or a vibrating bed for patients that are bed bound.

In one aspect of the present invention, a method of treating a patient with paralytic colon syndrome includes the following: urging the patient in a supported position to experience a vibration defined by an oscillating vertical displacement of at least three millimeters for at least ten minutes, wherein the oscillating vertical displacement is in a direction normal to a supporting surface of the supported position.

In another aspect of the present invention, the method of treating a patient with paralytic colon syndrome further includes wherein an oscillation of the oscillating vertical displacement vertical displacement has a frequency of at least five hertz, wherein the supported position is a seated position, wherein the patient is seated in a wheelchair, wherein at least one drive wheel of the wheelchair comprises a plurality of spaced apart protrusions, wherein each protrusion has an elevation, relative to a base exterior surface of the at least one drive wheel, that is between three to ten millimeters, whereby pushing the wheelchair results in the oscillating vertical displacement of the patient, wherein each two adjacent protrusions of the plurality of protrusions are spaced apart by at least three-hundred millimeters along the base exterior surface of the drive wheel, wherein each protrusion has a radial length of at least forty millimeters, or wherein pushing the wheelchair over an uneven surface result in the oscillating vertical displacement of the patient.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides a vibratory medical device to treat patients with paralytic colon syndrome, and a method of using the same by applying a forced vibration having a time-varying disturbance (load, displacement, velocity, or acceleration) is applied to a mechanical system.

The disturbance can be a periodic and steady-state input, a transient input, or a random input. The periodic input can be a harmonic or a non-harmonic disturbance with the response magnitude being dependent on the actual mechanical system.

Referring to FIGS. 1 through 8, an embodiment of the present invention provides a method for treating patients with paralytic colon syndrome by providing mechanical shaking or vibrating. The source of vibration is supplied mechanically by way of knobby tread or wave pattern tread on the wheels of a wheelchair being pushed along a supporting surface or with an electric motor that generates mechanical vibrations while the chair/seat is otherwise stationary.

For a manual push wheelchair, the special tires may need to be made per the specifications below. Though different material can be used to provide the "knobs" of the knobby tread, and wherein it is contemplated that sufficiently sized "mountain bike" tire for the wheelchair could enable the treatment claimed herein. The knobs used on the wheels are pronounced and each drop from the knob peak to the tire "valley" created a good deal of shake and vibration.

For a patient that is bedbound, a hospital bed enabled to generate mechanical vibrations may be used. Likewise, a lounge chair, with an operatively associated with an electric vibrator motor may facilitate the treatment plan.

Critically, the device provides ample/substantial vibration to the human body through the mechanical system that supports the weight of the human body. The same consideration is required for the device using an electric motor to create vibration.

Treatment includes that the patient riding in the wheelchair experiences a vibratory waveform or forced vibration of sufficient displacement and duration. For instance, as the knobby, wavy, or discontinuous surface of the tread impacts the supporting surface over which the wheelchair 10 travels, a vibratory shock is created resulting in the mechanical vibration sufficient to initiate peristaltic bowel movement. A motorized wheelchair would be preferable for sustaining the mechanical vibrations for extended periods.

Figure 7:
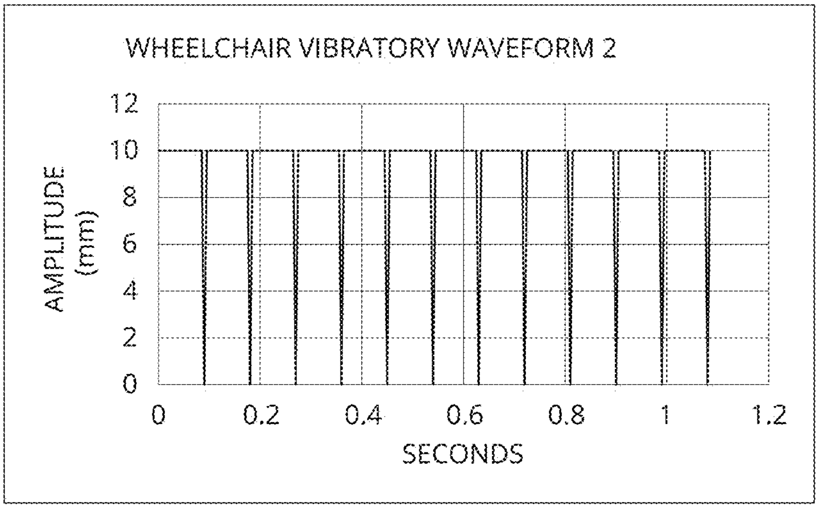
FIG. 7 is a diagrammatic view of an exemplary embodiment of a first vibratory waveform of the present invention.

Referring to FIG. 7, the present invention demonstrates through calculations of vibrations applied to a wheelchair that stimulated a patient's (who was diagnosed as having paralytic colon disease) colon by way of a first vibratory waveform that resulted in a properly functioning colon.

The below dimensions of the materials during the applications of the treatment method of the patient with paralytic colon disease produced the necessary vibration waveform to treat the patient.

Calculations:

Application 1: The wheel diameter is 610 mm. Perimeter=D*pi; P=1916 mm. Four protrusions or knobs were mounted equidistantly on each tire. Knobs are approximately 40 mm long×6 mm high. The wheelchair moved at a rate of 2236 mm per second.

The vibration was caused by the knobs. The distant between each knob/protrusion is calculated: 1916 mm/4 knobs=479 mm; 479 mm−40 mm (knob width)=439 mm. With a gap of 439 mm. So, every 439 mm the knob was contacted causing a 6 mm rise. That elevation lasted for 40 mm, then dropped 6 mm. The cycle would repeat itself.

In terms of time, the cycle calculations are:

$$439\text{ mm}/(2236\text{ mm/sec}) = 0.2\text{ sec}$$

$$40\text{ mm}/(2236\text{ mm/sec}) = 0.018\text{ sec}$$

Referring to FIG. 7, the present invention demonstrates a second vibratory waveform application created with a textured surface. The change in amplitude occurred as an instant spike of 10 mm. These occurred every 200 mm. The wheelchair also moved at a rate of 2236 mm/sec.

Figure 1:
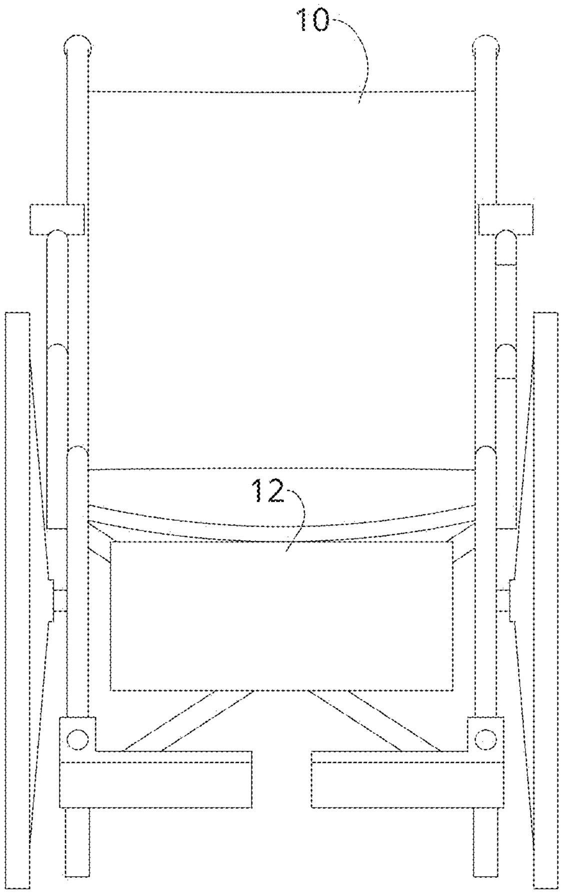
FIG. 1 is a front view of an exemplary embodiment of the present invention, illustrating placement of the motor 12; though it is understood that the motor 12 may be placed in other locations along the wheelchair 10, or that the wheelchair 10 could be remotely powered and still function as contemplated herein.
Figure 2:
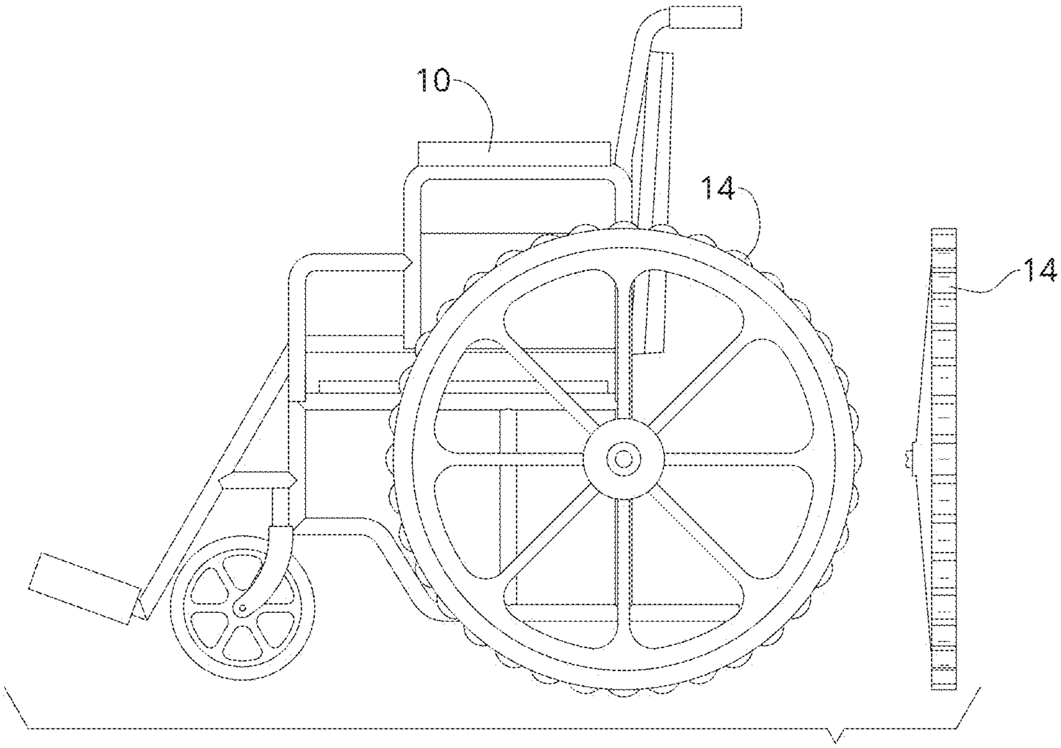
FIG. 2 is a side elevation view of the wheelchair 10 having a knobby tread 14, which is shown separately in an adjacent front elevation view.
Figure 3:
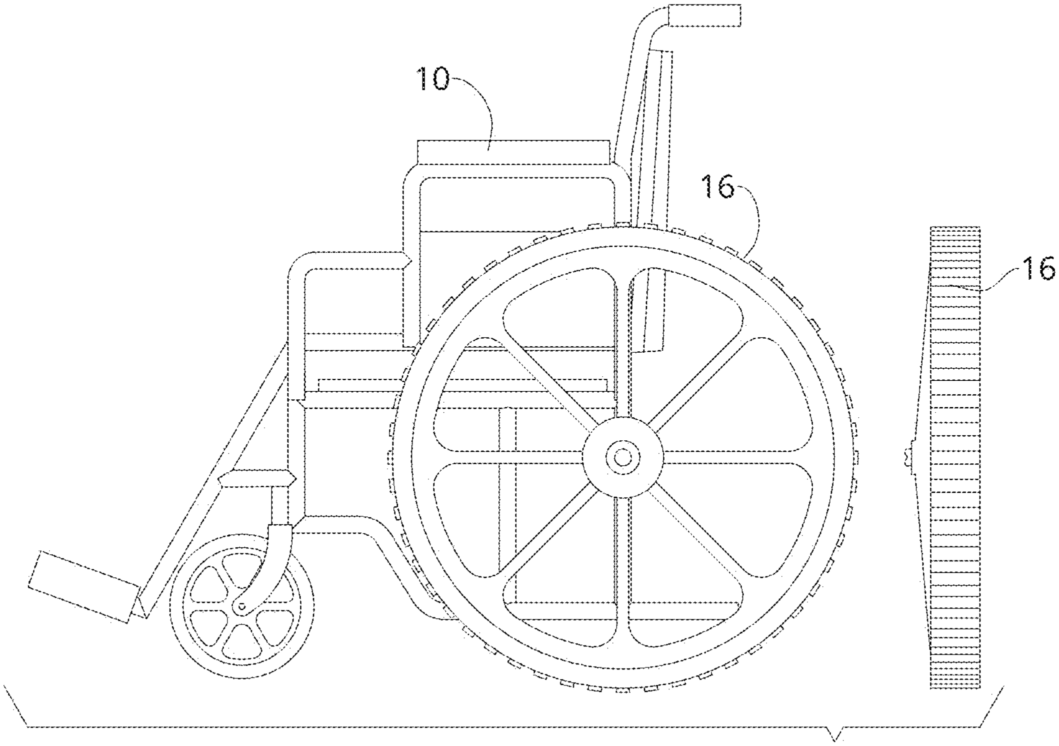
FIG. 3 is a side elevation view of the wheelchair 10 having an off-road tread 16, which is shown separately in an adjacent front elevation view.
Figure 4:
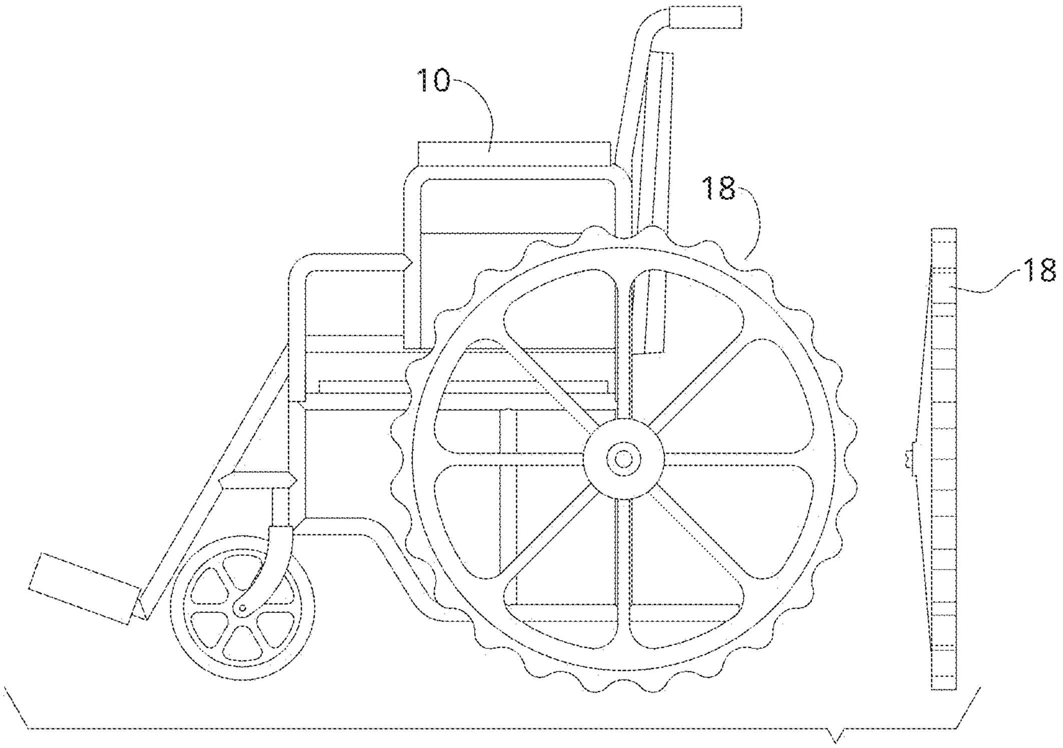
FIG. 4 is a side elevation view of the wheelchair 10 having a wavy tread 18, which is shown separately in an adjacent front elevation view.
Figure 5:
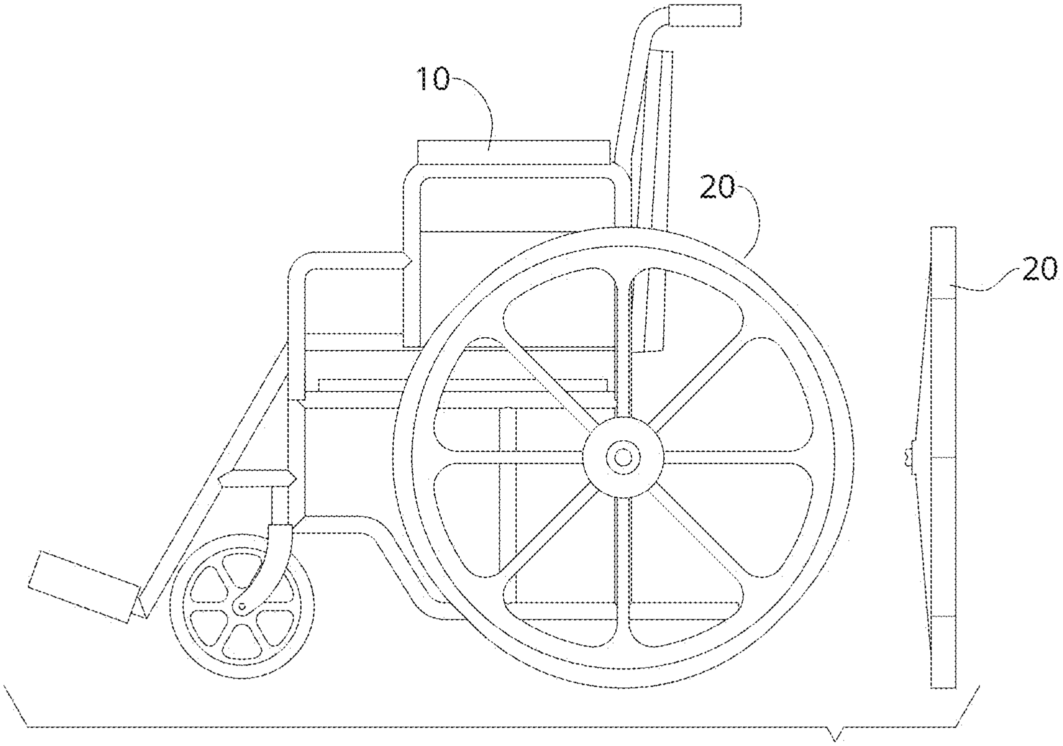
FIG. 5 is a side elevation view of the wheelchair 10 having a non-circular wheel 20, which is shown separately in an adjacent front elevation view.
Figure 6:
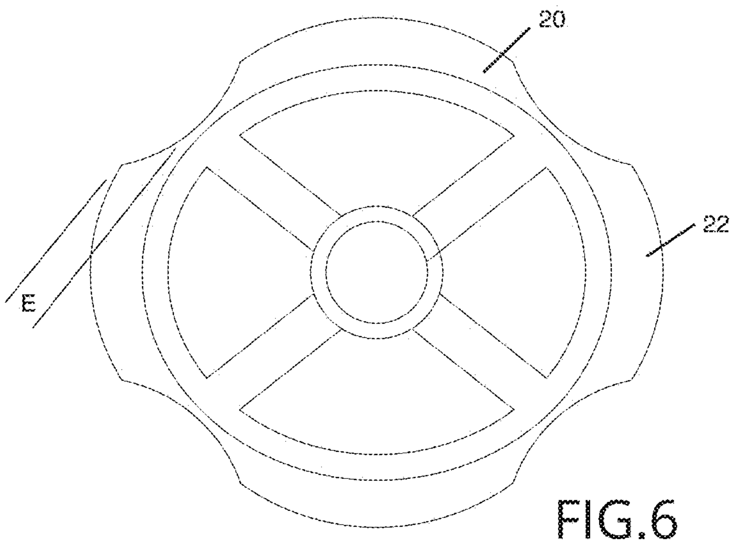
FIG. 6 is a detailed side elevation view of the non-circular wheel 20 of FIG. 5, illustrating the protrusions 22 comprising, in one embodiment, defined by a vertical displacement 'E', which is the relative elevation of the crest of a protrusion 22 relative to the trough disposed between two adjacent protrusions 22.
Figure 8:
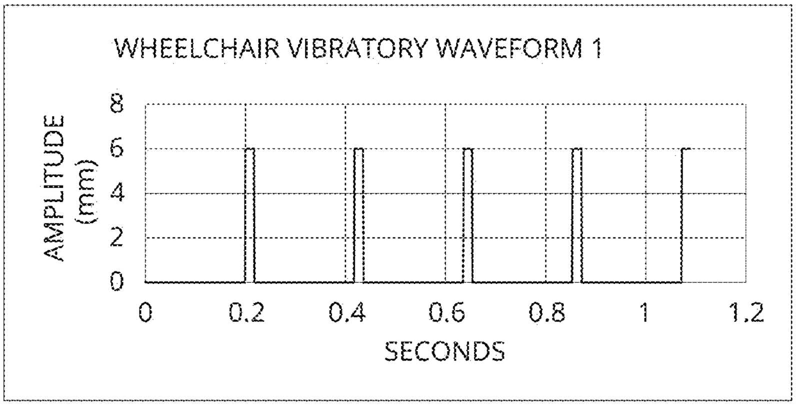
FIG. 8 is a diagrammatic view of an exemplary embodiment of a second vibratory waveform of the present invention.

The vibratory spikes occur according to the vibratory rate/vibratory waveform shown in FIG. 8: 200 mm/(2236 mm/sec)=0.09 sec. So, there are spikes every 0.09 seconds.

Additionally, the inventive methodologies disclosed herein could be used in other therapeutic recoveries.

As used in this application, the term "about" or "approximately" refers to a range of values within plus or minus 10% of the specified number. And the term "substantially" refers to up to 80% or more of an entirety. Recitation of ranges of values herein are not intended to be limiting, referring instead individually to any and all values falling within the range, unless otherwise indicated, and each separate value within such a range is incorporated into the specification as if it were individually recited herein.

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object. Further, for purposes of this disclosure, the term "mechanical communication" generally refers to components being in direct physical contact with each other or being in indirect physical contact with each other where movement of one component affect the position of the other.

The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "up," "down," and the like, are words of convenience and are not to be construed as limiting terms unless specifically stated to the contrary.

It should be understood, of course, that the foregoing relates to exemplary embodiments of the invention and that modifications may be made without departing from the spirit and scope of the invention as set forth in the following claims.

What is claimed is:

1. A method of treating a patient with paralytic colon syndrome, the method comprising:

seating the patient in a vibratory wheelchair so that a substantial portion of the weight of the patient is supported by a seat portion of the vibratory wheelchair; and selectively generating an oscillating vertical displacement of said seat portion of at least three millimeters relative to a supporting surface of the vibratory wheelchair for at least ten minutes by physically urging the vibratory wheelchair across the supporting surface, wherein the oscillating vertical displacement is in a direction normal to the supporting surface.

2. The method of claim 1, wherein an oscillation of the oscillating vertical displacement has a frequency of at least five hertz.

3. The method of claim 1, wherein the wheelchair comprises at least one drive wheel, and wherein the at least one drive wheel of the wheelchair comprises a plurality of spaced apart protrusions, wherein each protrusion has an elevation, relative to a base exterior surface of the at least one drive wheel, that is between three to ten millimeters.

4. The method of claim 3, wherein each two adjacent protrusions of the plurality of protrusions are spaced apart by at least three-hundred millimeters along the base exterior surface of the at least one drive wheel.

5. The method of claim 4, wherein each protrusion has a radial length of at least forty millimeters.

6. The method of claim 1, wherein the the supporting surface is an uneven surface.

7. A vibratory device for treating a patient with paralytic colon syndrome, the vibratory device comprising:

a wheelchair comprising at least one drive wheel, where the at least one drive wheel comprises:

a base exterior surface; and a plurality of spaced apart protrusions radially extending from an entirety of the base exterior surface, wherein each protrusion comprises a crest separated by two spaced apart concave troughs so that the crest has a crest elevation, relative to a lowest elevation of the two spaced apart concave troughs, that is between three to ten millimeters, whereby pushing the wheelchair results in an oscillating vertical displacement of the patient seated therein, whereby each concave trough is configured to engage uneven surfaces to achieve the oscillating vertical displacement.

* * * * *